United States Patent [19]

Bush

[11] 4,273,260

[45] Jun. 16, 1981

[54] DISPENSING OF FLUENT MATERIALS

[76] Inventor: George E. Bush, 65 Hillman St., Woodmead East, Sandton, Transvaal Province, South Africa

[21] Appl. No.: 6,145

[22] Filed: Jan. 24, 1979

[30] Foreign Application Priority Data

Feb. 3, 1978 [ZA] South Africa .................. 78/0674

[51] Int. Cl.³ ............................................. B67D 5/52
[52] U.S. Cl. ..................................... 222/135; 222/214; 222/309; 222/333; 128/215; 128/223; 417/476
[58] Field of Search ............... 222/206, 209, 214, 291, 222/372, 136, 138, 139, 142, 145, 309; 417/474–477; 128/DIG. 1, DIG. 18, 218 A, 215, 222–223; 138/118, 115–117

[56] References Cited

U.S. PATENT DOCUMENTS

| 2,696,173 | 12/1954 | Jensen | 417/477 |
| 2,898,859 | 8/1959 | Cornell | |
| 3,386,630 | 6/1968 | Haviland | 222/309 |
| 3,679,331 | 7/1972 | Kushner | 222/214 |
| 3,737,251 | 6/1973 | Berman et al. | 417/477 |
| 3,982,534 | 9/1976 | Buckman | 222/145 |
| 4,070,725 | 1/1978 | Austin et al. | 417/477 |
| 4,155,362 | 5/1979 | Jess | 417/477 |

Primary Examiner—H. Grant Skaggs
Attorney, Agent, or Firm—Donal B. Tobin

[57] ABSTRACT

A dispensing device for use in dispensing measured quantities of fluent materials through a plurality of resiliently compressible dispensing tubes, the device comprising a housing having a tube zone for receiving a plurality of dispensing tubes; collapsing device for collapsing, in compression zones, dispensing tubes when located in the tube zone; and displacement device for diplacing the collapsing device to advance the compression zones along compression paths to dispense fluent materials through such dispensing tubes, the compression paths being of differing effective lengths. A dispensing kit comprising a dispensing device as described, and a plurality of resiliently compressible dispensing tubes for location in the tube zone.

6 Claims, 8 Drawing Figures

DISPENSING OF FLUENT MATERIALS

This invention relates to the dispensing of fluent materials. More particularly, this invention relates to a dispensing device for use in dispensing fluent materials, and to a dispensing kit for use in dispensing fluent materials.

According to the invention, there is provided a dispensing device for use in dispensing measured quantities of fluent materials through a plurality of resiliently compressible dispensing tubes, the device comprising a housing having a tube zone for receiving a plurality of dispensing tubes; collapsing means for collapsing, in compression zones, dispensing tubes when located in the tube zone; and displacement means for displacing the collapsing means to advance the compression zones along compression paths to dispense fluent materials through such dispensing tubes, the compression paths being of differing effective lengths.

In an embodiment of the invention, the collapsing means may be adapted to be reciprocably displaced so that on its forward motion it will advance the compression zones along compression paths to dispense fluent material, and will then be returned to its initial position relatively to the tubes for subsequent operation.

In this embodiment of the invention, the dispensing device will include bias means to bias the collapsing means back to its inoperative or starting position.

In this embodiment of the invention, the housing may be adapted to locate the dispensing tubes along linear or substantially linear paths. If desired, however, the housing may be adapted to locate the tubes along curved paths.

In an alternative embodiment of the invention, the collapsing means may be pivotally displaceable.

Conveniently, the collapsing means may be rotatably displaceable, and the displacement means may be in the form of drive means for rotatably driving the collapsing means.

In this embodiment of the invention, the device may include control means for controlling operation of the drive means, the control means being adjustable to allow the collapsing means to be rotatably driven through a selected angle upon each actuation of the drive means.

Thus, for example, the control means may be adjustable to allow the collapsing means to be rotatably driven through a selected angle of less than 180°, through a selected angle of less than 360°, or through a selected angle of more than 360° upon each actuation of the drive means.

It will be appreciated that, if desired, the control means may be adjustable to allow the collapsing means to be rotatably driven through a selected number of revolutions upon each actuation of the drive means.

Thus by appropriately adjusting the control means, the extent of displacement of the collapsing means upon each actuation of the drive means, can be adjusted to adjust the quantities of fluent materials dispensed by the dispensing device upon each actuation of the drive means.

In an embodiment of the invention, the drive means may comprise a displaceable lever member.

The lever member may, for example, be in the form of a manually displaceable lever member, in the form of a foot operated lever member, or the like. The lever member may be reciprocably or pivotably displaceable.

In this embodiment of the invention, the control means may be adapted to control the extent by which the displaceable lever can be displaced upon actuation thereof, thereby controlling the angle through which the collapsing means is rotatably driven upon actuation of the lever member.

In an alternative embodiment of the invention, the drive means may comprise an electric motor adapted for connection to a suitable power source.

In this embodiment of the invention, the control means may again be operatively associated with the electric motor to control pivotal displacement of the electric motor upon actuation thereof, and thus the angle through which the collapsing means is rotatably driven upon actuation of the electric motor.

The electric motor may be adapted for connection to any suitable power source such as a mains outlet, a battery, a vehicle battery, a rechargeable battery mounted on the dispensing device, or the like.

In an embodiment of the invention, the differing effective lengths of the compression paths effected by the collapsing means during displacement thereof, may be provided by the device including a plurality of fixed cam members to co-operate with the collapsing means to define the effective lengths of the compression paths effected by the collapsing means during each revolution of the collapsing means.

In one example of the this embodiment of the invention, the collapsing means may comprise a plurality of separate collapsing members, and the cam members may be adapted to co-operate separately with the separate collapsing members to cause the collapsing members to be rotated eccentrically relatively to tubes located in the tube zone to define differing compression paths during each revolution of the collapsing means.

In an alternative embodiment of the invention the collapsing means may include a plurality of radially displaceable compression members which are slidably connected to the collapsing means, and the cam members may be adapted to cooperate with the respective compression members to define the effective lengths of the compression paths effected by the compression members.

In a further embodiment of the invention the compression members may be slidably connected to the collapsing means to project to differing extents beyond the periphery of the collapsing means for co-operating with dispensing tubes when located along different radii of curvature in the tube zone.

Each compression member may conveniently include bias means operative between it and the cam member to allow for manufacturing tolerances in the wall thicknesses of dispensing tubes being used in the dispensing device, to combat the compression member becoming jammed against a collapsed dispensing tube if the wall thicknesses of the tube are slightly oversize, and to combat the compression member failing to collapse a tube completely if the wall thicknesses of such a tube are slightly undersize.

In an alternative embodiment of the invention, the differing effective lengths of the compression paths may be provided by walls of the housing defining compression surfaces of differing effective lengths, against which the compression tubes are to be compressed during use.

The housing may conveniently have a supporting formation for supporting a dispensing nozzle on the housing.

The dispensing nozzle may be in the form of an oral dosing nozzle of any conventional type for oral administration of a veterinary remedy or the like. Alternatively, for dispensing a spot-on remedy, the dispensing nozzle may be in the form of a spot-on dispensing nozzle or lance of any conventional type.

The dispensing device may have any appropriate means for locating a plurality of dispensing tubes in the tube zone to combat axial displacement of the tubes during use.

In an embodiment of the invention, the housing may have dispensing tube inlet zones to co-operate with dispensing tubes to combat axial displacement of dispensing tubes located in the tube zone during use.

Alternatively, or additionally, the housing may include a removable cover plate for the tube zone, the cover plate having at least one securing flange to co-operate with walls defining the tube zone for securing dispensing tubes in position in the tube zone.

The invention further extends to a dispensing kit comprising a dispensing device as described herein, and a plurality of resiliently compressible dispensing tubes for location in the tube zone.

The dispensing tubes may conveniently have differing cross-sectional areas.

Where the housing has dispensing tube inlet zones, the dispensing tubes may have shoulder formations to co-operate with the dispensing tube inlet zones of the housing.

Where the housing includes a cover plate having at least one securing flange, the dispensing tubes may be connected to each other by means of connecting flanges, and at least one of the tubes may have an engagement flange for location between the securing flange of the cover plate and the walls defining the tube zone, for locating the tubes in position in the tube zone.

In an alternative embodiment, the tubes may be separate, and each tube may be provided with such an engagement flange.

Where the tubes do have such engagement flanges, conveniently only the portions of the tubes to be located in the tube zone, may have the flanges, and the remaining parts of the tubes connected to either end of those portions may be formed without the flanges, or may be formed separately and secured to those portions by means of a suitable adhesive.

The dispensing tubes may, if desired, be of eliptical cross-section to facilitate collapsing of the dispensing tubes by the collapsing means during use.

By having a dispensing tube of eliptical cross-section, it will be appreciated that by varying the length of the major axis of the cross-section of the tube, the volume of fluent material dispensed by the dispensing device during use, can effectively be varied.

While the dispensing tubes of this invention are resiliently compressible to allow them to recover after compression, their walls should not be so flexible that the tubes can expand or bulge unduly during use.

At least one dispensing tube may conveniently be connected to a collapsible fluent material container. It may conveniently be integrally connected to such a container.

The fluent material container may container a fluent material to be dispensed, so that the fluent material is housed in the container in a sterile condition when the dispensing tube is sealed by any suitable means, prior to use.

The dispensing tube and fluent material container containing the fluent material, can thus be supplied in a sterile sealed condition.

In an embodiment of the invention, the housing may have a dispensing nozzle integrally mounted thereon.

In an embodiment of the invention, where the fluent material is to be in the form of an injectable solution or an injectable slurry, the free end portions of the dispensing tubes may form a common discharge tube, and a needle or a floating needle may be operatively mounted at the free end of discharge tube.

In an embodiment of the invention, the floating needle may be integrally mounted on the tube, for disposal with the tube and fluent material container after use.

The needle, or the dispensing nozzle, as the case may be, may conveniently incorporate a one-way valve having a closure member which is biassed to combat dripping under the action of gravity when the device is not in use.

In an embodiment of the invention, the control means of the dispensing device may comprise a control circuit and a plurality of displaceable micro switches which are adapted to be actuated to actuate the control circuit, the control means being such that each displaceable switch will, upon actuation, cause the control means to allow the collapsing means to be rotatably driven through an angle which is specific for that displaceable switch.

In one example of this embodiment of the invention, the displaceable micro switches may be positioned at circumferentially spaced intervals for selective actuation by a pivotally displaceable control knob which is mounted on the device and has an actuating pointer mounted thereon.

Usually, the dispensing device of this invention will be used for dispensing two different liquids or slurries in a required proportion to each other. It will be appreciated however, that this invention can equally be applied to the dispensing of fluent materials from three or more tubes in desired proportions.

The dispensing device of this invention may be in the form of a gun with a handle portion to allow it to be handled for use.

In an alternative embodiment of the invention, the dispensing device of this invention may be in the form of a unit to be placed at a suitable location or to be suspended on the body of an operator.

In this embodiment of the invention, the device may include an actuating member which may be actuated at a point remote from the device to actuate the device.

The actuating member may include a needle or a dispensing nozzle, may be of a suitable shape to be held by hand, and may have the free ends of the dispensing tubes or the free end of a common discharge tube located therein.

This invention can have application wherever to or more fluent materials are to be dispensed in desired relative proportions, particularly where the fluent materials are required to be dispensed in particular successive dosages.

Thus, for example, the invention can have application in dispensing different chemical substances, in dispensing veterinary remedies, pesticides, toxic substances, dosing materials, medicines, and the like.

In conventional applications for veterinary remedies and the like, the usual concentrations which would be desirable, would require dilution of between about 4:1 and 10:1 by volume with water. Dilutions of this order can readily be effected by appropriate selection of effective compression lengths and/or tube cross-sectional areas.

In an embodiment of the invention, a back pack may be used in the dispensing kit, which has separate compartments, the one for containing the active ingredient, and the other for containing the diluent or the substance to be mixed with the active ingredient.

In an embodiment of the invention, where the device is to be used for oral dosing of a veterinary remedy, the dispensing device may be set so that the active ingredient will be mixed with the required proportion of water during portion of the cycle of the collapsing means, whereafter no further active ingredient will be dispensed during the remainder of the cycle, but water alone will be dispensed to serve as a purging dose and combat loss of active ingredient as a result of spitting.

Embodiments of the invention are now described by way of example with reference to the accompanying drawings.

In the drawings

Figure 1:
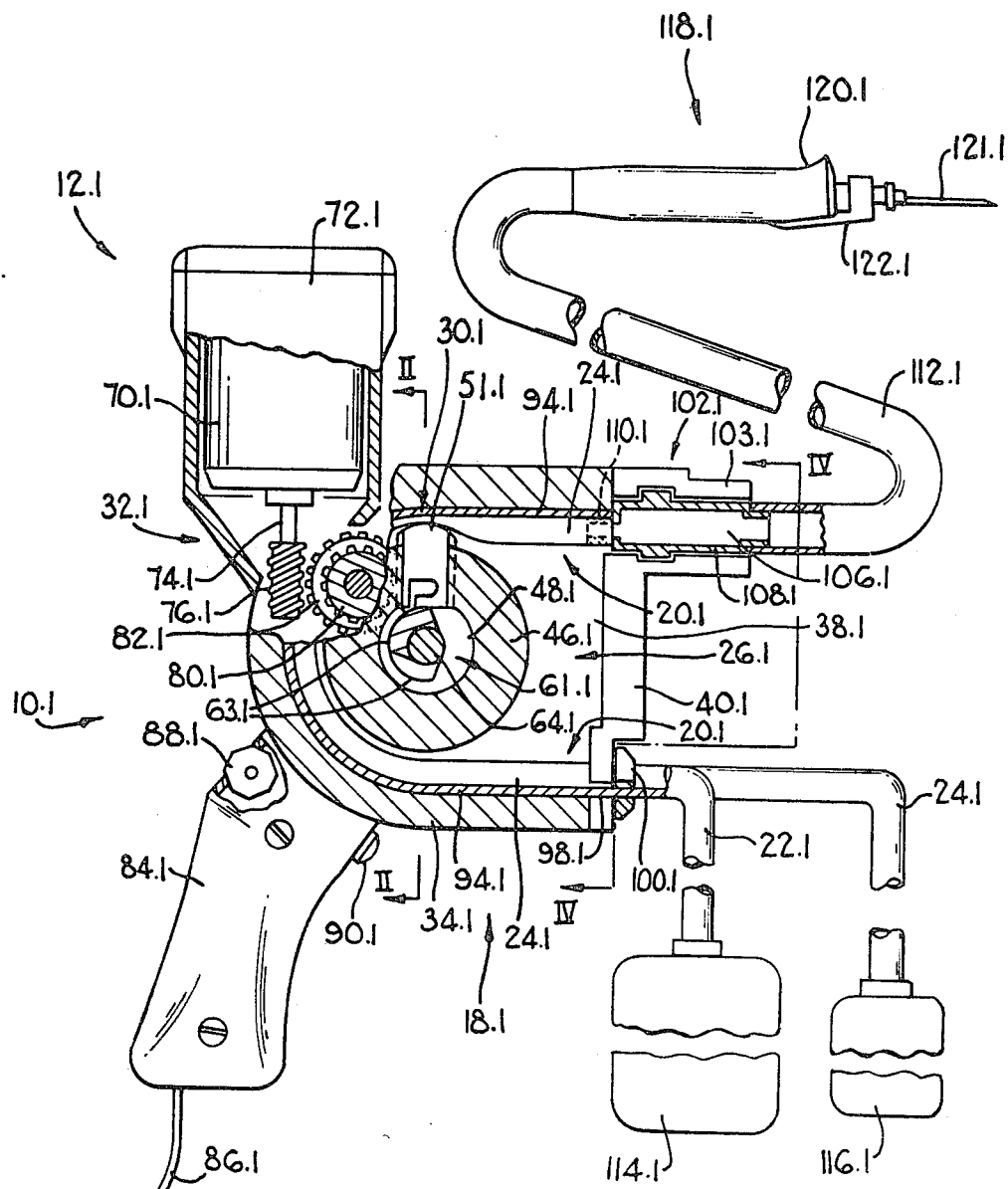
FIG. 1 shows a diagrammatic, fragmentary, partly sectional side elevation along line I—I of FIG. 2, of one embodiment of a dispensing kit in accordance with this invention for use in dispensing measured quantities of fluent materials through two resiliently compressible dispensing tubes.

With reference to FIGS. 1 to 4 of the drawings, reference numeral 10.1 refers generally to a dispensing device for use in dispensing measured quantities of fluent materials through two resiliently compressible dispensing tubes.

Reference numeral 12.1 refers generally to a dispensing kit in accordance with this invention, comprising the dispensing device 10.1, removably loaded with two resiliently compressible dispensing tubes 22.1 and 24.1.

The dispensing kit 12.1 is suitable for use in dispensing a veterinary remedy which is provided in concentrated form, simultaneously with a diluent in the form of water, in predetermined portions so that the diluted veterinary remedy which is dispensed, will be at the correct concentration for a required dosage rate.

It will be appreciated, however, that the dispensing kit 12.1 may be used in the same way for dispensing two different veterinary remedies simultaneously.

The dispensing device 10.1 comprises a housing 18.1 having a tube zone 20.1 for removably receiving the two resiliently compressible dispensing tubes 22.1 and 24.1.

The dispensing devcie 10.1 further comprises collapsing means 26.1 for collapsing, in compression zones 28.1 and 30.1, the dispensing tubes 22.1 and 24.1 when located in the tube zone 20.1; and displacement means in the form of drive means 32.1 for rotatably displacing the collapsing means 26.1 to advance the compression zones 28.1 and 30.1 along compression paths to dispense fluent materials through the dispensing tubes 22.1 and 24.1.

The tube zone 20.1 is defined by a peripheral compression wall 34.1, by a locating shoulder 36.1 along a base wall 38.1, by a front wall 40.1, and by a removable cover plate 42.1 having a locating flange 43.1.

The removable cover plate 42.1 has a knob 44.1 which can be held for applying or removing the cover plate 42.1.

Once the tubes 22.1 and 24.1 have been located in position in the tube zone 20.1, the cover plate 42.1 can be fixed to the housing 18.1 to close the tube zone 20.1.

The dispensing device 10.1 includes a securing screw (not shown) for securing the cover plate 42.1 in its operative position.

The collapsing means 26.1 comprises a single rotary member 46.1 having a hollow bore 48.1.

The rotary member 46.1 has two axially spaced radially displaceable compression members 50.1 and 51.1 slidably mounted thereon for displacement in the radial direction relatively to the axis of the rotary member 46.1.

Figure 3:
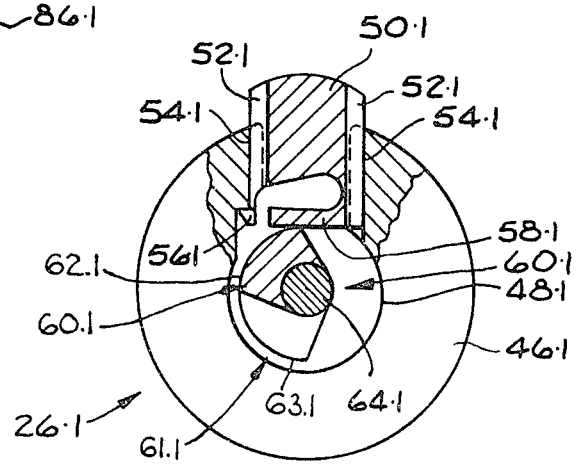
FIG. 3 shows, to an enlarged scale, a fragmentary, partly sectional side elevation of the collapsing means and the cam means of the dispensing device of the dispensing kit of FIGS. 1 and 2.

As can be seen in particular in FIG. 3, each of the compression members 50.1 and 51.1 has opposed flanges 52.1 which are slidably located in complementary slots 54.1 in the rotary member 46.1 to allow the axially spaced compression members 50.1 and 51.1 to be slidably displaced in the radial direction.

Each compression member 50.1 and 51.1 has a hook 56.1 which co-operates with the rotary member 46.1 to locate the compression member 50.1 and 51.1 against complete withdrawal from the rotary member 46.1.

Each compression member 50.1 and 51.1 is formed with a resilient portion 58.1 which is resiliently flexible to serve the purpose as will be hereinafter described.

Each compression member 50.1 and 51.1 is formed out of a self-lubricating synthetic plastics material to reduce frictional resistance between it and the dispensing tubes 22.1 or 24.1, as the case may be, during use. If desired, however, a suitable lubricant may be applied to the portions of the dispensing tubes 22.1 and 24.1 which will co-operate with the compression members 50.1 and 51.1, prior to use of the tubes.

The dispensing device 10.1 further includes two fixed cam members 60.1 and 61.1 to cooperate with the compression members 50.1 and 51.1 respectively to define the effective lengths of the compression paths effected by the compression members 50.1 and 51.1 during rotational displacement of the rotary member 46.1.

The cam member 60.1 has a camming surface 62.1 extending through an angle of 90°. The cam member 61.1 has a camming surface 63.1 extending through an angle of 180°.

The cam members 60.1 and 61.1 with their camming surfaces 62.1 and 63.1 are located within the hollow bore 48.1 and are mounted on a fixed shaft 64.1 which extends therefrom through a suitable bore in the housing 18.1.

The adjustment shaft 64.1 is fixed in position by means of a screw 66.1.

Figure 2:
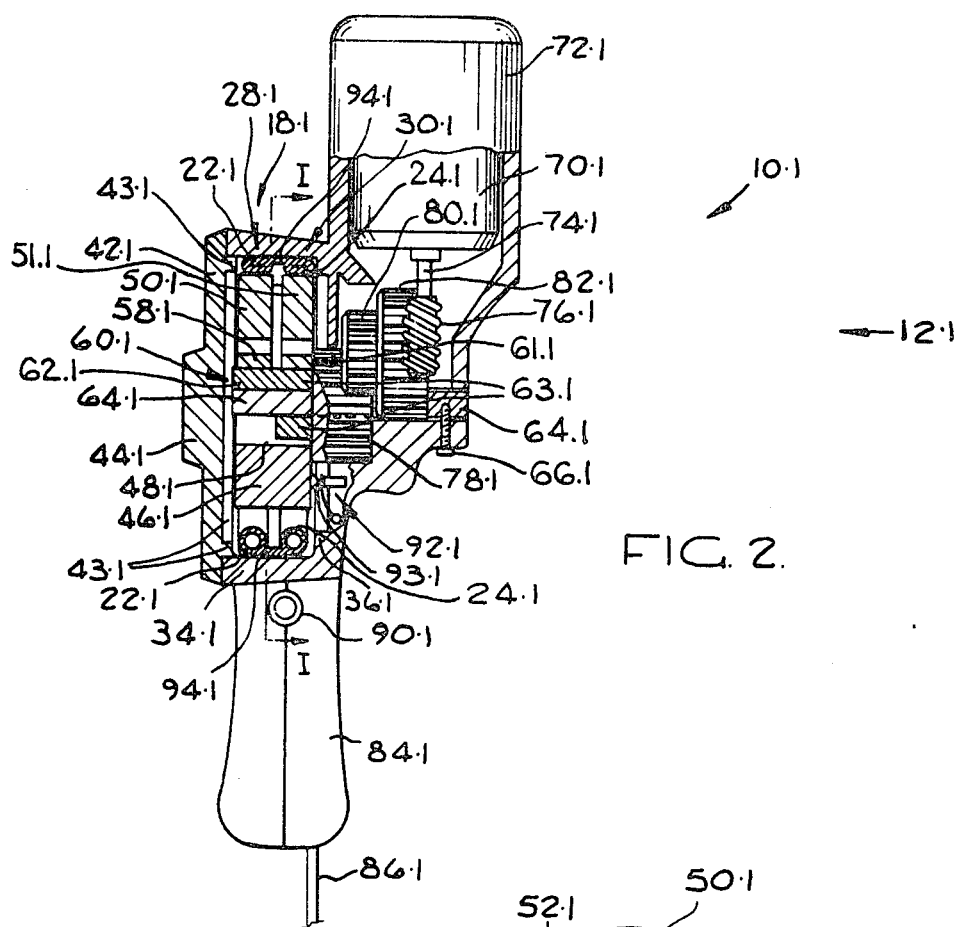
FIG. 2 shows a diagrammatic, fragmentary, partly sectional front elevation along line II—II of FIG. 1, of the dispensing kit of FIG. 1.
Figure 4:
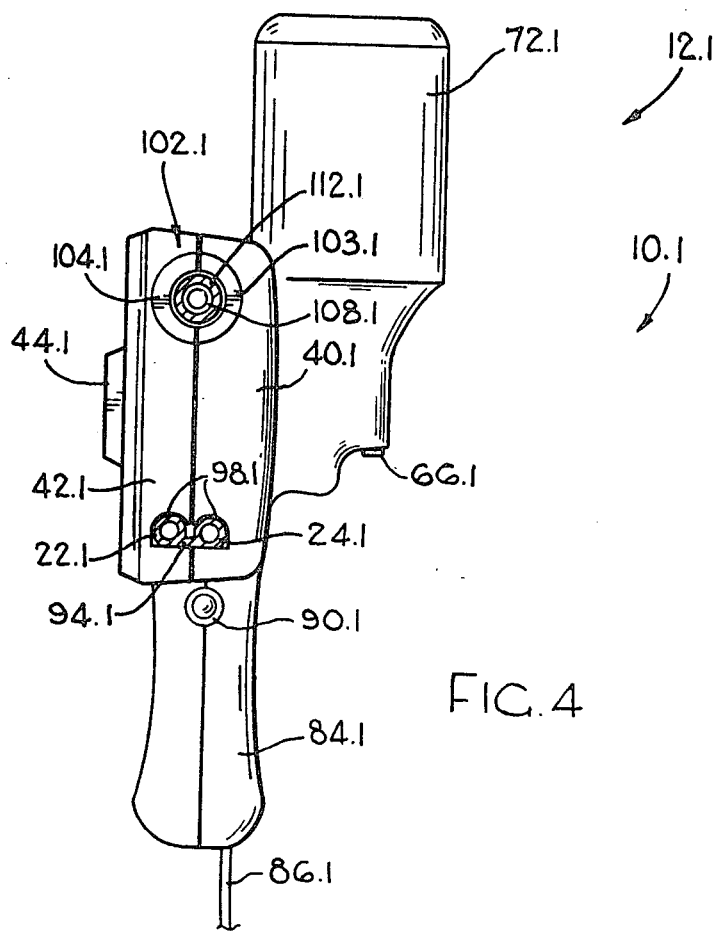
FIG. 4 shows a diagrammatic, fregmentary, sectional front elevation along line IV—IV of FIG. 1, of the dispensing kit of FIG. 1.

In use, if the rotary member 46.1 is rotatably driven by the drive means 32.1, the compression member 50.1 will co-operate with the camming surface 62.1 so that the camming surface will force the compression member against the tube 22.1 to collapse the tube in a compression zone 28.1 horizontally to the left of the central axis of the cam member 60.1 when the rotary member 46.1 is rotated in a clockwise direction, as viewed in FIG. 1. Thereafter, the compression zone 28.1 will be advanced by the compression member 50.1 through an arc of 90° until the compression member 50.1 reaches the position vertically above the axis of the cam member 60.1, as shown in FIGS. 1, 2 and 4.

At the same time, the compression member 51.1 will cooperate with the camming surface 63.1 so that the camming surface will force the compression member against the tube 24.1 to collapse the tube in a compression zone 30.1 vertically below the central axis of the cam member 61.1 when the rotary member 46.1 is rotated in a clockwise direction. Thereafter the compression zone 30.1 will be advanced by the compression member 51.1 through an arc of 180° until the compression member 51.1 reaches the position vertically above the axis of the cam member 61.1.

It follows that the quantities of fluent materials dispensed through the tube 22.1 during each revolution of the rotary member 46.1 will be half the quantity dispensed through the tube 24.1 since the compression path for the tube 22.1 extends through an arc of only 90° whereas that for the tube 24.1 extends through an arc of 180°.

In this way, the quantities of fluent materials dispensed through the tubes 22.1 and 24.1 on each revolution of the rotary member 46.1, are varied.

The camming surfaces 62.1 and 63.1 co-operate with the resilient portions 58.1 to displace the compression members 50.1 and 51.1 radially outwardly during use.

The resilient portions 58.1 therefore allow for manufacturing tolerances in the wall thicknesses of the dispensing tubes 22.1 and 24.1 to combat the compression members becoming jammed against the collapsed tubes if the wall thicknesses are slightly oversize, and to combat failure to collapse the tubes sufficiently if the wall thicknesses of the tubes are slightly undersize.

The drive means 32.1 as illustrated in the drawings, comprises an electric motor 70.1 mounted in a motor housing 72.1 which extends upwardly from the housing 18.1. The motor 70.1 has a drive shaft 74.1 extending therefrom, and a gear 76.1 is mounted on the drive shaft.

The rotary member 46.1 has an annular gear 78.1 provided thereon below the hollow bore 48.1. The annular gear 78.1 has a bore through which the adjustment shaft slidably extends.

The annular gear 78.1 and the gear 76.1 are operatively coupled by means of a gear train 80.1 and 82.1.

The dispensing device 10.1 includes a handle 84.1 which is integral with the housing 18.1. The handle 84.1 is shaped and the size and mass of the dispensing device 10.1 are such that it can readily be held in one hand for use.

An electrical lead 86.1 extends out of the handle 84.1 for connecting the motor 70.1 to a suitable source of electrical power.

The dispensing device 10.1 includes control means which is mounted in the handle 84.1 for controlling operation of the motor 70.1 to allow the motor to rotatably drive the rotary member 46.1 through a selected number of revolutions upon each actuation of the motor 70.1.

The control means comprises a control circuit of any suitable conventional type, which includes a plurality of displaceable micro switches (not shown) which are adapted to be selectively actuated to actuate the control circuit, the control means being such that each displaceable switch will, on actuation, cause the control means to allow the motor 70.1 to rotatably drive the rotary member 46.1 through a number of revolutions specific for that displaceable switch.

The displaceable mirco switches are mounted at circumferentially spaced intervals for selective actuation by a pivotally displaceable control knob 88.1 (FIG. 1) which is mounted in the handle 84.1 and which has an actuating pointer for actuating the micro switches.

In the embodiment illustrated in the drawings, the control circuit includes seven micro switches, and the control knob 88.1 has eight stations. The control knob 88.1 can thus be positioned in a first station where none of the micro switches are actuated, in a second station where the micro switch which will cause a single revolution of the rotary member 46.1 is actuated, and so on until the eighth station where, upon actuation of the control circuit, the rotary member 46.1 will be driven through seven revolutions.

The control circuit includes an actuating trigger 90.1 which is mounted on the handle 84.1 for actuating the control circuit.

The control circuit further includes a counter of conventional type to count the number of revolutions of the rotary member 46.1 upon actuation of the control circuit, to allow the control circuit to cease operation once the dictated number of revolutions have occurred.

The counter is actuated by means of a micro switch 92.1 (as shown only in FIG. 2) in the base wall 38.1.

The rotary member 46.1 has a pointer 93.1 (as shown in FIG. 2), mounted on its lower surface to actuate the micro switch 92.1 once during each revolution.

Thus, by suitably setting the control knob 88.1, the dispensing device 10.1 can be operated by actuation of the trigger 90.1, so that a desired number of revolutions are performed by the rotary member 46.1 for each actuation of the trigger. Thus, desired quantities of fluent material can be dispensed upon each actuation of the trigger 90.1.

Those portions of the dispensing tubes 22.1 and 24.1 which are located in the tube zone 20.1, are integrally connected to each other by means of a connecting flange 94.1.

The device 10.1 has inlet threading apertures 98.1 which are defined partly by the housing 18.1 and partly by the cover plate 42.1 (FIG. 4). The dispensing tubes 22.1 and 24.1 are provided with shoulder formations 100.1 to cooperate with the inlet threading apertures 98.1 to combat axial displacement of the tubes during use.

The device 10.1 has a supporting formation 102.1 which is constituted by a semi-circular trough 103.1 defined by the housing 18.1, and by a complementary trough 104.1 defined by the cover plate 42.1, to co-operate with and complete the supporting formation 102.1.

The dispensing tubes 22.1 and 24.1 form part of a fluent material pack for use with the dispensing device 10.1, as shown in FIG. 1.

The fluent material pack includes a mixing chamber 106.1 defined by a casing 108.1. The casing has inlet sleeves 110.1 (only one being visible) which lead to the mixing chamber 106.1, and to which the discharge ends of the tubes 22.1 and 24.1 are connected. A single discharge tube 112.1 extends from the casing 108.1.

The casing 108.1 defining the mixing chamber 106.1 has a complementary shape to that of the supporting formation 102.1. Thus, when the tubes are located in the tube zone 20.1, the casing 108.1 will be located in the trough 102.1. When the cover plate 42.1 has been fixed in position, the casing 108.1 will be firmly located in the complete supporting formation 102.1.

The dispensing tubes 22.1 and 24.1 are formed out of a resiliently compressible synthetic plastics material and are of a convenient length for effective use. The synthetic plastics material is such that the tubes can be resiliently compressed during use, and will recover after compression, but the material is not so flexible that the tubes will expand or bulge unduly under pressure.

With particular reference to FIG. 1 of the drawings, the fluent material pack comprises the dispensing tubes 22.1 and 24.1, and two collapsible fluent material containers 114.1 and 116.1.

The dispensing tube 22.1 is sealingly connected to the container 114.1 whereas the tube 24.1 is sealingly connected to the container 116.1.

The container 116.1 contains water, whereas the container 114.1 contains the required veterinary remedy.

Instead of the container 116.1 being in the form of a collapsible container, it may be in the form of a rigid container which may be suspended on the body of an operator.

Where the container is rigid, it may have a filling opening with a closure cap which allows air to bleed into the container during use, thereby combatting the establishment of a reduced pressure within the container.

In use, a selected veterinary remedy can be provided in the container 114.1 in a sterile condition. Thereafter the dispensing tube 22.1 can be fixed to the container 114.1.

Once the tube 22.1 has been sealed, the veterinary remedy will be stored in the container 114.1 in a sterile condition.

When the system is required for use, the tube 24.1 can be sealingly connected to the container 116.1 which is filled with water which is sufficiently sterile.

The fluent material pack will therefore remain sterile until it is required for use. Since the veterinary remedy is provided in a concentrated form in the collapsible container 114.1, this will reduce the cost of transport and will further facilitate sterilisation of the remedy to combat deterioration during storage or transportation, and prior to use.

While the tubes 22.1 and 24.1 are shown in FIGS. 1 to 4 as having the same bore area, it will be appreciated that tubes of differing bore area may be used.

Thus, by selecting the tubes 22.1 and 24.1 with an appropriate cross-sectional bore area relationship between them, when the fluent material pack is used, the concentrated veterinary remedy and the water from the containers 114.1 and 116.1 respectively, will be dispensed in a definite and predetermined proportion.

Thus, the concentrated veterinary remedy will be diluted in the appropriate proportion, and dilution will occur in the mixing chamber 106.1 immediately prior to use of the diluted veterinary remedy.

Even if the water is therefore contaminated to the extent that it can cause deterioration of the veterinary remedy, this will not be material since the diluted remedy is used immediately it is mixed with water, and is otherwise maintained completely separate from the water.

It is therefore an advantage of the embodiment of the invention as illustrated in FIGS. 1 to 4 of the drawings that a veterinary remedy can be stored in a concentrated and sterile condition and yet is readily available for use.

The embodiment as illustrated provides the further advantage that the veterinary remedy can be supplied as part of the fluent material pack thereby permitting use without any undue risk of skin contact with the veterinary remedy.

The embodiment as illustrated in the drawings can provide the further advantage that by appropriate selection of the cross-sectional areas of the dispensing tubes 22.1 and 24.1, it can be ensured that dilution of the concentrated veterinary remedy will be effected automatically and in the correct proportions, and that contamination of the veterinary remedy and the dangers of physical contact on dilution or mixing, can be reduced if not totally eliminated.

The embodiment of the invention as illustrated in the drawings provides the further advantage that by means of the control circuit and the control knob 88.1, the quantity of diluted veterinary remedy dispensed for each actuation of the control circuit by means of the trigger 90.1, can be readily and effectively adjusted over a reasonable range.

In practice therefore, it will be necessary to ensure that the concentration of the veterinary remedy is appropriate in relation to the relationship between the bore cross-sectional areas and the effective compression lengths of the dispensing tubes 24.1 and 22.1 so that the concentrated veterinary remedy will be diluted in the appropriate proportion during use. Thereafter, by appropriate adjustment of the control knob 88.1, the dosage rate can be varied over a wide range to cater for the usual range of dosage rates which will be required during use.

The embodiment of the invention as illustrated in these Figures of the drawings, provides the further advantage that since the compression members 50.1 and 51.1 co-operate slidably with the dispensing tubes under the biassing action of the resilient portions 58.1, they should not tend to be subject to undue wear. If the tubes 22.1 and 24.1 do become worn, this is of no consequence since they should last for a sufficient period to allow the active ingredient contained in the container 114.1 to be dispensed, and can then be discarded.

This can therefore provide the further advantage that even abrasive slurries and the like can be dispensed by means of the dispensing kit 12.1.

In an alternative embodiment of the invention, if it is found that a compression member 50.1 or 51.1 does become subject to wear, it can instead be replaced by a more robust biassing arrangement than the resilient portion 58.1 and, in addition, a roller may be mounted at the operative end of the compression member 50.1 or 51.1 to co-operate with the dispensing tubes.

The discharge tube 112.1 has a floating needle 118.1 sealingly mounted at its free end. The floating needle therefore forms a further part of the fluent material pack.

The floating needle 118.1 is shaped to be conveniently handled by hand, and has a thumb-receiving flange 120.1.

The floating needle 118.1 has a spring-biassed one-way valve (not shown) located within its bore to combat discharge of fluent material under the action of gravity when the fluent material pack is not in use.

The floating needle 118.1 is shown having a conventional needle 121.1 mounted thereon by means of a conventional type of threaded cap 122.1.

The threaded cap 122.1 may conveniently be such that prior to fitting of the needle 120.1, the floating needle 118.1 will be sealed by the threaded cap. Thus, the fluent material pack comprising the collapsible container 114.1, the dispensing tubes 22.1 and 24.1, and the floating needle 118.1 will be maintained in a sealed hygienic condition for storage and transportation prior to use. It will be appreciated that if the container 116.1 is not fixed to the tube 24.1, the tube 24.2 will also be appropriately sealed prior to use.

The embodiment of the invention as illustrated in FIGS. 1 to 4 of the drawings, can therefore provide the further advantage that once the veterinary remedy contained in the container 114.1 has been used up, the fluent material pack can be disposed of entirely. In this way inadvertent use of a contaminated remedy, and re-use of a contaminated fluent material pack or any components thereof, will tend to be avoided.

Figure 5:
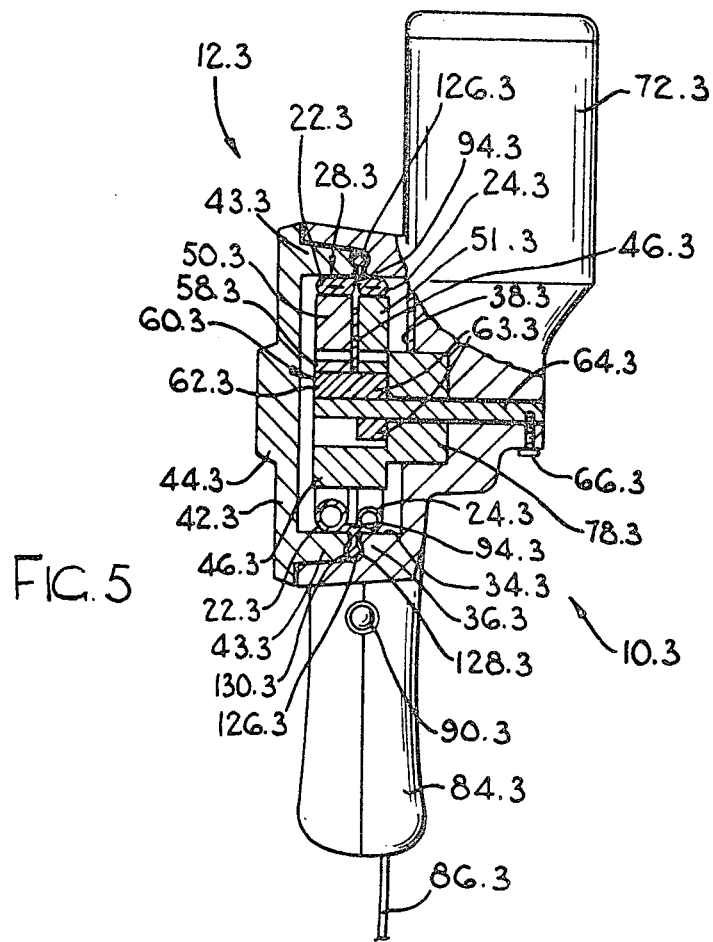
FIG. 5 shows a diagrammatic, partly sectional, front elevation of an alternative embodiment of a dispensing kit in accordance with this invention.

With reference to FIG. 5 of the drawings, reference numeral 12.3 refers generally to an alternative embodiment of a dispensing kit in accordance with this invention. The dispensing kit 12.3 corresponds substantially with the dispensing kit 12.1 and corresponding parts are therefore indicated by corresponding reference numerals, except that the suffix '.3' has been used in place of the suffix '.1'.

The dispensing kit 12.3 differs from the kit 12.1 in that positive securing means is provided for securing the tubes in position in the tube zone 20.3.

The two tubes 22.3 and 24.3 are integrally connected to each other by means of a connecting flange 94.3.

The connecting flange 94.3 has an engagement flange 126.3 integrally formed therewith.

The tube zone 20.3 is defined by a locating shoulder 36.3 which constitutes a compression wall 34.3 for one of the tubes, and which has a securing formation 128.3 along its surface directed away from the base wall 38.3.

The tube zone 20.3 is further defined by the cover plate 42.3 having a securing flange 43.3 projecting therefrom.

The securing flange 43.3 has a securing formation 130.3 provided along its surface directed away from the cover plate 42.3.

The securing formation 130.3 corresponds with and is complementary to the securing formation 128.3.

For locating the dispensing tubes 22.3 and 24.3 in the tube zone 20.3, the engagement flange 126.3 can be positioned in the securing formation 128.3. Thereafter the cover plate 42.3 can be fitted with the securing formation 130.3 co-operating with the securing formation 128.3 to trap and locate the engagement flange 126.3 between them.

When the cover plate 42.3 is secured in position, the engagement flange 126.3 and thus the tubes 22.3 and 24.3 will be held securely and firmly in the tube zone 20.3 and, in particular, will be held firmly and securely against axial displacement during use.

The embodiment of the invention as illustrated in FIG. 5 of the drawings therefore provides the advantage that the tubes can be easily and securely located in the tube zone for effective use, and can readily be removed when required.

It will be appreciated that, in this embodiment the locating flange 43.3 defines a compression surface for the other tube.

Figure 6:
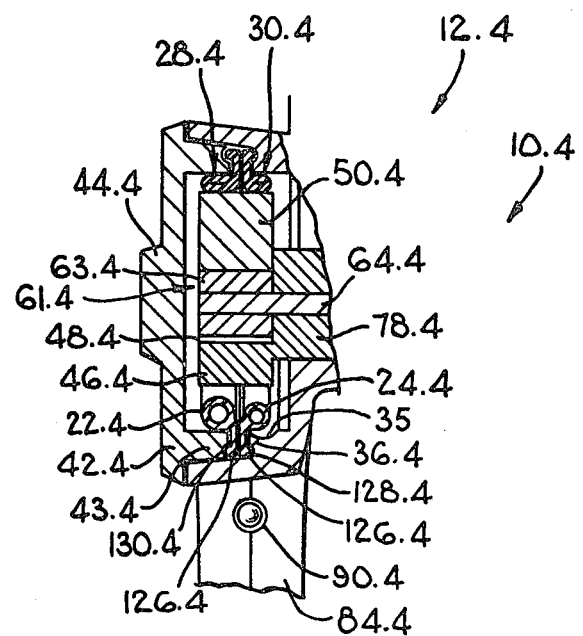
FIG. 6 shows a fragmentary view corresponding to that of FIG. 5, of yet a further alternative embodiment of a dispensing kit in accordance with this invention.

With reference to FIG. 6 of the drawings, reference numeral 12.4 refers to yet a further alternative embodiment of a dispensing kit in accordance with this invention.

The dispensing kit 12.4 corresponds substantially with the dispensing kit 12.3 and corresponding parts are therefore indicated by corresponding reference numerals, except that the suffix '0.4' is used instead of the suffix '0.3'.

In the dispensing kit 12.4, the dispensing tubes 22.4 and 24.4 are separate, but each one has an engagement flange 126.4 integrally formed therewith to serve the same purpose as the single engagement flange 126.3, for locating the tubes in the tube zone 20.4.

In the kit 12.4, the compression wall 34.4 is shown having a trough shaped recess 35 which is in register with the tube 24.4 and which extends through an arc of 90°. The effect of the recess 35 is therefore to reduce effective length of the compression path for the tube 24.4 to an arc of 90° as opposed to a compression path for the tube 22.4 which extends through an arc of 180°.

In the dispensing kit 12.4, because of the differing effective lengths of the compression paths presented by the compression surfaces, the device 10.4 includes a single cam member 61.4 having a single camming surface 63.4 which extends through an arc of 180°, and has a single collapsing member 50.4 to cooperate with the camming surface 63.4.

Thus during each revolution of the rotary member 46.4, the collapsing member 50.4 will cooperate with both dispensing tubes, but the tube 22.4 will be compressed through an arc of 180° whereas the tube 24.4 will only be compressed through an arc of 90°.

The embodiment of the invention as illustrated in FIG. 6 of the drawings therefore provides the advantage that the dispensing tubes can be firmly and securely located in the tube zone, and that the effective lengths of the tubes which are presented for compression during use are different because of the compression surfaces being of differing lengths.

Figure 7:
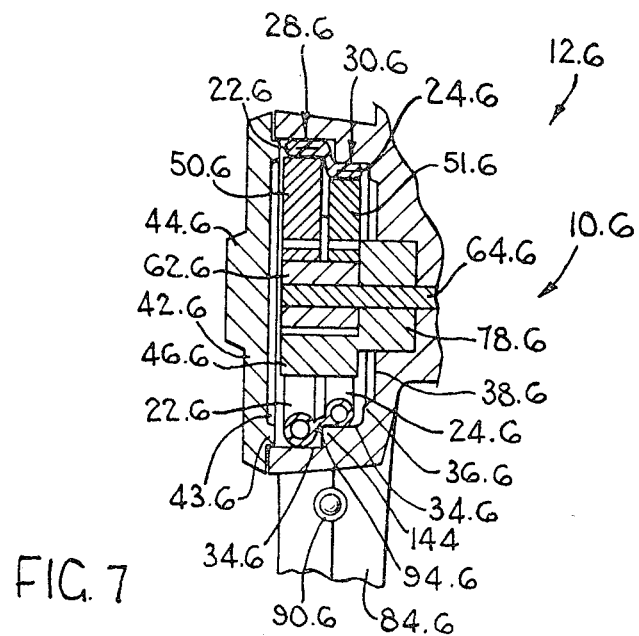
FIG. 7 shows a fragmentary view corresponding to that of FIG. 5 of yet a further alternative embodiment of a dispensing kit in accordance with this invention.

With reference to FIG. 7 of the drawings, reference numeral 12.6 refers generally to yet a further alternative embodiment of a dispensing kit in accordance with this invention.

The dispensing kit 12.6 corresponds substantially with the dispensing kit 12.1, and corresponding parts are therefore indicated by corresponding reference numerals, except that the suffix '0.6' is used instead of the suffix '0.1'.

In the dispensing kit 12.6, the dispensing device 10.6 has a single cam member 60.6 which has a camming surface 62.6 extending through an arc of 180°. However, the rotary member 46.6 has a pair of radially displaceable compression members 50.6 and 51.6 mounted on the rotary member 46.6 in axially spaced positions.

The compression members 50.6 and 51.6 thus both co-operate with the cam member 60.6.

The compression members 50.6 and 51.6 project to differing extents beyond the periphery of the rotary member 46.6 for co-operating with dispensing tubes 22.6 and 24.6 which are located along different radii of curvature in the tube zone.

The compression wall 34.6 is shaped to define a stepped configuration for locating the dispensing tubes along different radii of curvature.

Thus, the compression wall 34.6 has a locating shoulder 36.6 to define one end of the tube zone, the cover plate 42.6 has a locating formation 43.6 to define the opposed end of the tube zone, and the compression wall 34.6 has a step 144 which supports the dispensing tube 24.6 at a radius of curvature which is less than that at which the dispensing tube 22.6 is supported.

The dispensing tubes 22.6 and 24.6 are integrally connected by means of a connecting flange 94.6 of an appropriate configuration to co-operate with the step 144.

Since the dispensing tubes 22.4 and 24.4 are located along different radii of curvature, their effective lengths presented for compression by the compression members 51.4 and 50.4 during use, will be different.

Thus, as in the case of the dispensing kit 12.4, the relative proportions of fluent materials dispensed through the dispensing tubes during use will depend not only on the relative proportions of their cross-sectional areas, but also on the relative proportions of their effective lengths presented for compression.

Figure 8:
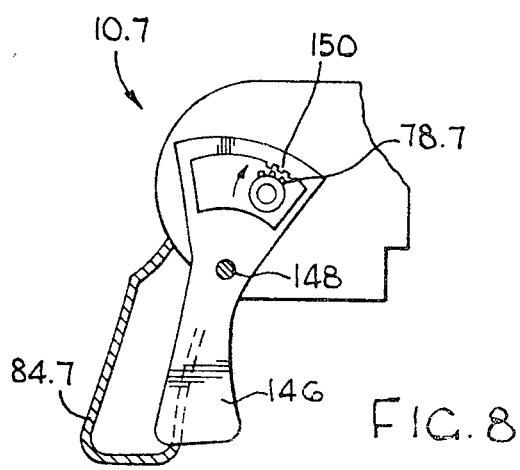
FIG. 8 shows a fragmentary, diagrammatic view of yet a further alternative embodiment of a dispensing device in accordance with this invention.

With reference to FIG. 8 of the drawings, reference numeral 10.7 refers generally to an alternative embodiment of a dispensing device in accordance with the invention.

The dispensing device 10.7 corresponds generally with the dispensing device 10.1 except that in place of the drive means 32.1, the dispensing device 10.7 includes a manually operable lever 146 for displacing the collapsing means during use.

The lever 146 is pivotally mounted in the handle 84.7 about a pivot pin 148.

The lever 146 is provided with a linear gear 150 to co-operate with the annular gear 78.7 of the rotary member of the dispensing device 10.7.

The lever 146 includes a return spring (not shown) to return the lever to its starting position. It further includes a suitable directional clutch or the like (not shown), to release the annular gear 78.7 from the rotary member during return of the lever 146 to its starting position.

In use, when the handle 84.7 is held in the hand of an operator, finger pressure can be applied to the lever 146 to displace it about the pivot pin 148. During such displacement the linear gear 150 co-operates with the annular gear 78.7 to rotatably drive the annular gear 78.7 and thus the rotary member of the dispensing device 10.7.

It will be appreciated that there are practical limitations on the extent to which displacement of the lever 146 can rotate the rotary member of the dispensing device 10.7. In practice, therefore, unless a complex gear train system is employed, it may be found that for each displacement of the lever 146, it is only practical to have the rotary member rotatably driven through one revolution or possibly two revolutions.

The embodiments of the invention as illustrated in the drawings, can provide the further advantage that where only portion of the concentrated veterinary remedy has been used, the fluent material pack can be resealed for later use without that remaining portion having become contaminated or diluted with water. Thus, the preservatives remaining in that remaining portion of the concentrated veterinary remedy should therefore be sufficient to preserve it for future use.

While the embodiments of the invention as illustrated in the drawings, have been described with reference to the dilution of a veterinary remedy which is applied as an injectable solution, as an oral dosing solution or as a spot-on solution, it will be appreciated that the dispensing kit of this invention may be applied equally to the dispensing of various other types of fluent materials. In addition, it may be used not merely for dilution but also for the mixing of different fluent materials in appropriate proportions.

It follows from the embodiments of the invention as illustrated in the drawings, that the relative proportions of fluent materials dispensed through the dispensing tube by means of the dispensing kit of this invention, may be varied by using dispensing tubes of differing cross-sectional areas, and by using tubes having differing effective compression lengths.

In practice, particularly for veterinary remedies, the simplest procedure would probably tend to be to provide each active ingredient which is to be dispensed, in a desired concentration form for dilution when it is dispensed, and then selecting tube cross-sectional bore areas which will provide for the proportion of active ingredient to water dispensed during use to be in the correct relationship.

I claim:

1. A dispensing device for use in dispensing measured quantities of fluent material through a plurality of resiliently compressible dispensing tubes, the device comprising:

a housing having a tube zone for receiving a plurality of dispensing tubes;

collapsing means for collapsing, in compression zones, dispensing tubes when located in the tube zone;

said collapsing means including a plurality of displaceable compression members slidably connected to said collapsing means and projecting to different extents beyond the periphery of said collapsing means for cooperating with the dispensing tubes when located along different radii of curvature in the tube zone;

displacement means for displacing the collapsing means to advance the compression zones along compression paths to dispense fluent materials through said dispensing tubes, the compression paths being of different effective lengths;

a plurality of fixed cam members to cooperate with said collapsing means to define the effective length of the compression paths affected by the collapsing means during operation of the collapsing means;

said cam members being adapted to cooperate with the respective compression members to define the effective lengths of the compression paths affected by the compression members.

2. A device according to claim 1, in which the collapsing means is rotatably displaceable, and in which the displacement means comprises drive means for rotatably driving the collapsing means.

3. A device according to claim 1, in which the drive means comprises a displaceable lever member.

4. A device according to any one of claim 1, in which the housing has dispensing tube inlet zones to co-operate with dispensing tubes to combat axial displacement of dispensing tubes located in the tube zone during use.

5. A device according to any one of claim 1, in which the housing includes a removable cover plate for the tube zone, the cover plate having at least one securing flange to co-operate with walls defining the tube zone for securing dispensing tubes in position in the tube zone.

6. A device according to claim 1, in which the housing has a supporting formation for supporting a dispensing nozzle on the housing.

* * * * *